United States Patent
Kruse et al.

(10) Patent No.: US 8,304,237 B2
(45) Date of Patent: Nov. 6, 2012

(54) METHOD AND DEVICE FOR FORMING BIOLOGIC CELL AGGREGATES

(75) Inventors: Charli Kruse, Herrnburg (DE); Sandra Danner, Luebeck (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 12/665,325

(22) PCT Filed: Jun. 13, 2008

(86) PCT No.: PCT/EP2008/004798
§ 371 (c)(1),
(2), (4) Date: Dec. 17, 2009

(87) PCT Pub. No.: WO2008/155072
PCT Pub. Date: Dec. 24, 2008

(65) Prior Publication Data
US 2010/0184621 A1 Jul. 22, 2010

(30) Foreign Application Priority Data
Jun. 20, 2007 (DE) .......................... 10 2007 028 423

(51) Int. Cl.
*C12N 5/00* (2006.01)
*C12N 5/02* (2006.01)

(52) U.S. Cl. ........ 435/395; 435/377; 435/378; 435/379; 435/402

(58) Field of Classification Search .................. None
See application file for complete search history.

(56) References Cited

U.S. PATENT DOCUMENTS

| | | | |
|---|---|---|---|
| 5,427,742 A | 6/1995 | Holland | |
| 5,650,164 A | 7/1997 | Della Valle et al. | |
| 5,792,653 A | 8/1998 | Weibezahn et al. | |
| 2008/0064034 A1 | 3/2008 | Kruse et al. | |

FOREIGN PATENT DOCUMENTS

| | | |
|---|---|---|
| DE | 4132379 A1 | 4/1993 |
| DE | 69522448 T2 | 6/2002 |
| DE | 10311981 A1 | 9/2004 |
| DE | 10242066 B4 | 3/2005 |
| DE | 102004062216 A1 | 7/2006 |

(Continued)

OTHER PUBLICATIONS

Definition of "continuous" in Merriam Webster's Collegiate Dictionary, tenth edition, 1996, at p. 251.*

(Continued)

*Primary Examiner* — Anne-Marie Falk
(74) *Attorney, Agent, or Firm* — Caesar, Rivise, Bernstein, Cohen & Pokotilow, Ltd.

(57) ABSTRACT

The invention relates to a method for cultivating biologic cells (1), wherein cells (1) are grown on a substrate (10) having a plurality of substrate openings (11), and wherein cell aggregates (2) are formed, including groups of cells (1) that span the substrate openings (11). A separation of the cell aggregates (2) from the substrate (10) by extracting the cell aggregates (2) from the substrate openings (11) can be provided. The invention further relates to a cell-cultivating device (100), including a substrate (10) having a plurality of substrate openings (11) and cell aggregates (2) including groups of cells (1) that span the substrate openings (11). The cell aggregates (2) are particularly used in high throughput tests with biologically active substances or in methods of tissue cultivation.

14 Claims, 2 Drawing Sheets

A

B

FOREIGN PATENT DOCUMENTS

| | | |
|---|---|---|
| EP | 0759064 B1 | 8/2001 |
| WO | 9700314 A1 | 1/1997 |
| WO | 9728252 A1 | 8/1997 |
| WO | 2004027017 A1 | 4/2004 |
| WO | 2004081514 A3 | 9/2004 |
| WO | 2005114178 A1 | 12/2005 |
| WO | 2006069752 A3 | 7/2006 |
| WO | 2006093207 A1 | 9/2006 |

OTHER PUBLICATIONS

Danner et al., "Derivation of oocyte-like cells from a clonal pancreatic stem cell line", Mol. Hum. Reprod., (2006), pp. 1-10.

Folch et al., "Microengineering of Cellular Interaction", Annu. Rev. Biomed. Eng., vol. 2 (2000), pp. 227-256.

Fukuda et al., "Orderly Arrangement of Hepatocyte Spheroids on a Microfabricated Chip", Tissue Engineering, vol. 11 (2005), pp. 1254-1262.

Guldner et al., "Autonomously contracting human cardiomyocytes generated from adult pancreatic stem cells and enhanced in co-cultures with myocardial biopsies", The International Journal of Artificial Organs, vol. 29 (2006), pp. 1158-1166.

Karp et al., "Controlling size, shape and homogeneity of embroyoid bodies using poly(ethylene glycol) microwells", Lab Chip, vol. 7 (2007), pp. 786-794.

Konno et al., "Photo-immobilization of a phospholipid polymer for surface modification", Biomaterials, vol. 26 (2005), pp. 1381-1388.

Kruse et al., "Adult pancreatic stem/progenitor cells spontaneously differentiate in vitro into multiple cell lineages and form teratoma-like structures", Ann. Anat., vol. 188 (2006); pp. 503-517.

Kruse et al., "Pluripotency of adult stem cells derived from human and rat pancreas", Appl. Phys. A, (2004), pp. 1617-1624.

Lin et al., "Long-term maintenance of liver-specific functions in three-dimensional culture of adult rat hepatocytes with a porous gelatin sponge support", Biotechnol. Appl. Biochem., vol. 21 (1995), pp. 19-27.

Napolitano et al., "Dynamics of the Self-Assembly of Complex Cellular Aggregates on Micromolded Nonadhesive Hydrogels", Tissue Engineering, vol. 13 (2007), pp. 2087-2095.

Park et al., "Microfabrication-based modulation of embryonic stem cell differentiation", Lab Chip, vol. 7 (2007), pp. 1018-1028.

Pollock et al., "Formation of Spheroidal Aggregates of Hepatocytes on Biodegradable Polymers Under Continuous-Flow Bioreactor Conditions", Eur. J. Pediatr. Surg., vol. 8 (1998), pp. 195-199.

Seaberg et al., "Clonal identification of multipotent precursors from adult mouse pancreas that generate neural and pancreatic lineages", Nature Biotechnology, 22(9) (2004), pp. 1115-1124.

Seeberger et al., "Expansion of mesenchymal stem cells from human pancreatic ductal epithelium", Laboratory Investigation, vol. 86 (2006), pp. 141-153.

Sodunke et al., "Micropatterns of Matrigel for three-dimensional epithelial cultures", Biomaterials, vol. 28 (2007), pp. 4006-4016.

\* cited by examiner ial cells,
METHOD AND DEVICE FOR FORMING BIOLOGIC CELL AGGREGATES

BACKGROUND OF THE INVENTION

The invention relates to a method for culturing biological cells, in particular a method for forming biological cell aggregates, and to a cell culturing device.

It is generally known to culture biological cells outside an organism (in vitro culturing). Typically the cells form a cell culture on a plastics or glass substrate in a culturing medium. For example, a growth and/or differentiation of the cells is provided on the substrate. In numerous cell biology methods the task is that of removing groups of cells from the cell culture, for example in order to subject these groups to further culturing or to an analysis. In conventional standard cell biology methods, groups of cells are removed from a cell culture using mechanical means (e.g. using a separating tool) or using chemical means (e.g. by enzymatic degradation).

With in vitro culturing on a substrate, the cells typically form a bed of cells having few layers of cells or having only a single layer of cells (monolayer). The formation of thin layers presents a problem if large groups of cells are required for study or further culturing. In this case the cells must be separated from the substrate over a relatively large surface area. This can lead to undesirable biochemical reactions which impair the subsequent method steps.

For specific cell types or culturing media, growth beyond the monolayer can be achieved in individual cases. The cells form three-dimensional cell aggregates. For example, in the adherent state stem cells form cell aggregates (what are known as "organoid bodies", see C. Kruse et al. in Appl. Phys. A, vol. 79, 2004, p. 1617-1624; and C. Kruse et al. in Ann. Anat., vol. 188(6), 2006, p. 503-517).

The above-mentioned standard cell biology methods can likewise be used to separate three-dimensional cell aggregates from a cell culture. In practice, however, the problem with this is that the cell aggregates are not uniformly formed on the substrate. On the conventionally used substrates, the cell aggregates form an inhomogeneous distribution, in particular in respect of the geometric arrangement and size of the cell aggregates. Furthermore, the typically spontaneously formed cell aggregates are at different stages of development. Thus a cell aggregate can include specific differentiated cells, while a younger cell aggregate does not include these cells. In practice, however, there is often interest in removing from a cell culture, for subsequent method steps, a plurality of cell aggregates having characteristics that are as similar as possible, in particular having, as far as possible, the same size and shape and the same stage of development. Thus hundreds or thousands of cell specimens of the same type are required for high-throughput test methods where e.g. the biological action of a pharmacological substance is studied.

A further limitation of the conventional culturing techniques relates to the shape of the cell aggregates. Cell aggregates are combined into larger aggregate formations for the provision of tissue models for study purposes or for the formation of implants in what is known as "tissue engineering". There is thus interest in the cell aggregates having a specific shape to make it easier to combine the aggregate formation. Using the conventional mechanical means, however, cell aggregates can be shaped only with considerable effort, while shaping is virtually impossible where cells are enzymatically degraded from a cell culture.

Thus only small groups of cells which are too small for further method steps, or cell aggregates having undesirably heterogeneous characteristics can be obtained from a cell culture using the conventional standard cell biology methods.

It is also known to culture biological cells on porous substrates (e.g. EP 0 759 064 B1, WO 97/00314). A porous substrate allows the cells to be controlled, e.g. with an active substance, from the substrate side. Conventional porous substrates have such small pore sizes that a cell covers over a pore (see e.g. DE 10 2004 062 216 A1). Handling of the cells on porous substrates poses the same problems as those mentioned above in relation to the standard methods of in vitro culturing.

The objective of the invention is that of providing an improved method for culturing biological cells, a method with which the problems and limitations of conventional methods are overcome. The objective of the invention is also that of providing an improved device for culturing biological cells, a device with which disadvantages of conventional culturing techniques are overcome.

These objectives are achieved by means of a method and/or a cell culturing device of the invention.

SUMMARY OF THE INVENTION

According to a first aspect, the objective of the invention is achieved by means of the general technical teaching of providing a method for culturing biological cells wherein there are formed from the cells on a substrate, the surface of which has substrate openings, cell aggregates which are arranged in the substrate openings. The inventors found that substrates having substrate openings are overgrown by living cells such that groups of cells span the substrate openings. The groups of cells form cell aggregates. The cell aggregates, which comprise a combination of the biological cells, e.g. in the form of organoid bodies, are self-supportingly formed on the substrate openings. In each case, one of the substrate openings is spanned by a group of cells forming one cell aggregate.

Advantageously, the geometric characteristics of the substrate, in particular the size and distribution of the substrate openings, create culturing conditions with which the size and distribution of the cell aggregates are controlled, in particular determined. Unlike the inhomogeneous formation of cell aggregates on conventional substrates with continuous surfaces, the cell culturing according to the invention results in a distribution of the cell aggregates corresponding to the arrangement of the substrate openings. Furthermore, it has advantageously been found that the cell aggregates in the substrate openings can each grow in a similar size. If the cells are provided simultaneously on the substrate, the cell aggregates can develop simultaneously. According to the invention, similar cell aggregates of defined size and/or development stages can thus be produced in large numbers in parallel, such as are required, for example, for research purposes, in particular in the case of high-throughput tests.

According to a second aspect, the objective of the invention is achieved by the general technical teaching of providing a cell culturing device having a substrate with substrate openings and having cell aggregates which span the substrate openings. Advantageously, the cell culturing device according to the invention forms a reservoir of cell aggregates with predetermined geometric characteristics. The cell culturing device can be used as a source of specimens for cell biology methods such as, for example, cell culturing, in particular the formation of aggregate formations, or cell investigations.

Here the term "substrate" generally designates a component that is suitable as a support for biological cells. The substrate comprises a substrate body having at least one substrate surface adapted for receiving the biological cells and perforated by the substrate openings. Sections of the substrate body that adjoin the substrate openings are also referred to here as "substrate elements". The substrate body has a planar extension and is made of a solid material which can be rigid or flexible.

According to a preferred embodiment of the culturing method according to the invention, separation of the cell aggregates from the substrate is provided, in particular by means of mechanical extraction of the cell aggregates from at least one of the substrate openings. Advantageously, by comparison with conventional culturing on continuous substrate surfaces the cell aggregates have fewer bonds between cells and the solid substrate material. Thus, far fewer cells are damaged and correspondingly fewer undesirable biochemical reactions are induced when the cell aggregates are separated from the substrate. The biochemical state of the cell aggregates is virtually unaffected by the separation from the substrate, and this is again advantageous for subsequent method steps such as, for example, further culturing or tests on the cell aggregates.

For the separation of the cell aggregates from the substrate, the cell culturing device according to the invention preferably has a separating device with at least one separating tool, preferably with a plurality of separating tools which are matched at least to a subset of the substrate openings of the substrate. The separating tools have a geometric arrangement identical to the geometric distribution of at least a portion of the substrate openings.

According to a first variant of the invention, the separation of the cell aggregates can comprise extraction from the substrate openings. In this case the cell aggregates are advantageously completely separated from the substrate material. For the extraction of the cell aggregates the separating device preferably has stamping tools. Each stamping tool comprises a projection that is formed on a tool body and that is adapted for pressing a cell aggregate through and out of one of the substrate openings.

The extraction of the cell aggregates from the substrate openings advantageously, according to a further embodiment of the invention, allows the substrate openings to be overgrown with further cells such that, after the extraction of a first generation of cell aggregates and new overgrowth with cells, a further generation of cell aggregates is formed. These can again be separated from the substrate and be subjected to further method steps. It is particularly preferably possible to achieve a cyclic process wherein a continuous substrate consisting of a flexible material circulates past the separating device. The cell aggregates are repeatedly formed in the substrate openings of the circulating substrate and are detached from the substrate when they pass the separating device.

According to a second variant of the invention, the cell aggregates can be separated together with substrate elements which adjoin at least one substrate opening. In this case the separating device can act solely on the substrate elements such that any undesirable effect on the cell aggregates can be reduced. In subsequent method steps the substrate elements removed with the cell aggregates from the substrate can be resorbed by the cells, mechanically separated or dissolved by a separately added substance. For the separation of the cell aggregates in combination with the substrate elements, the separating tools of the separating device preferably comprise punching elements having an arrangement identical to the geometric distribution of the substrate elements surrounding the substrate openings.

According to a further variant of the invention, the cell aggregates can be separated from the substrate using a cutting device having, for example, a scalpel. This embodiment is preferably achieved with a compact substrate, in the surface of which the substrate openings are provided as depressions.

According to a particularly preferred embodiment of the invention, a plurality of cell aggregates are separated from the substrate simultaneously. Advantageously, this allows all the cell aggregates to be in the same geometric and/or biological state at the moment of separation. In dependence on the requirements for the use of the invention, it is thus also possible to provide biologically identical cell aggregates in a number exceeding 10, e.g. 50 or 100, for high-throughput tests even 500 or 1000.

For culturing purposes the cell aggregates separated from the substrate are preferably transferred onto a target substrate and there subjected to further culturing (in particular growth and/or differentiation). The form of the target substrate can be freely selected. It can, for example, have a common substrate surface for all cell aggregates or a plurality of separate compartments, each of which receives a cell aggregate or a group of cell aggregates. Joining of the cell aggregates on the target substrate into aggregate formations is particularly preferred for uses in histogenesis.

According to an advantageous use of the invention, the cell aggregates are formed in a first culturing vessel, detached from the substrate and moved with the target substrate into a second culturing vessel, thereby avoiding undesirable mechanical or enzymatic effects on the cells.

A further advantage of the invention is based on the great flexibility available in the choice and design of the substrate. For example, the substrate can have a compact substrate body, in the substrate surface of which the substrate openings are formed as depressions. The cell aggregates are self-supportingly formed in the substrate opening. In this case the good stability of the substrate and the protection of the cell aggregate from the substrate body side are advantageous. Alternatively, the substrate can have a substrate body in which the substrate openings are throughgoingly formed from one surface to the other surface. The substrate body is in the form of a straight or curved plate or film with throughgoing holes. In this case, advantageously interactions of the cells with the substrate material are minimized and the cells in the substrate openings can be more easily supplied with culturing medium. The culturing medium can be supplied to the cells on both sides. The substrate can, in particular, be in the form of a net or lattice, the meshes of which forming the substrate openings. Furthermore, the substrate elements can have predetermined breaking points adjoining the substrate openings. These variants are particularly advantageous for the joint detachment of cell aggregates and substrate elements from the substrate.

For the formation of a cyclic process with a circulating substrate it may be advantageous for the substrate to have a thickness of less than 3 mm. The small thickness can improve the flexibility of the substrate and, where the latter is formed with throughgoing substrate openings, can improve the supply of culturing medium to the cells. The substrate is preferably made from a biologically inert material, in particular a plastic, e.g. nylon, polystyrene, polypropylene, nitrocellulose, polyethylene terephthalate, a noble metal, e.g. gold or platinum, or a resorbable material, e.g. fibrin.

The size of the substrate openings is preferably selected such that the cells can overgrow the free space of the substrate openings from the adjoining substrate elements, and such that there is enough room for the cultured cell aggregates in the substrate openings. A typical dimension of the substrate opening (e.g. diameter or edge length) is selected, for example, in the range from 5 µm, preferably greater than 100 µm, e.g. greater than 150 µm, to 1 mm. A cell aggregate arranged in the substrate opening may include at least 5 cells, preferably at least 100 cells, e.g. over 1000, such as, for example, 100,000 cells.

Advantageously, the substrate openings can also be used to form the cell aggregates with a predetermined aggregate shape. The cross-sectional shape of the substrate opening is impressed on the cell aggregate. This embodiment of the invention is advantageous, in particular, for culturing uses, in particular in tissue engineering.

According to the invention, preferably stem cells (not human embryonic stem cells), in particular adult stem cells, particularly preferably glandular adult stem cells, are cultured on the substrate having the substrate openings. Glandular adult stem cells are described e.g. by N. W. Guldner et al. in "Int. J. Artif. Organs", vol. 29(12), 2006, p. 1158-66; S. Danner et al. in "Mol. Hum. Reprod.", vol. 13(1), 2007, p. 11-20; C. Kruse et al. in "Appl. Phys.", vol. 79, 2004, p. 1617-1624; R. M. Seaberg et al. in "Nat. Biotechnol.", vol. 22(9), 2004, p. 1115-1124; and K. L. Seeberger et al. in "Lab. Invest.", vol. 86(2), 2006, p. 141-153. The inventors found that stem cells are particularly well suited to the culturing according to the invention on the basis of the following characteristics. First, stem cells have the capacity to overgrow substrates and to form thereon three-dimensional aggregates (organoid bodies). The three-dimensional aggregates can be continuously replicated from adherent stem cells.

This is advantageous, in particular, for the repeated formation of cell aggregates on substrate openings.

The use of cell aggregates that have been formed using the method according to the invention for a high-throughput test with biologically active substances, e.g. for a pharmacological high-throughput test, or for tissue culture, e.g. for tissue engineering, constitutes an independent subject of the invention.

BRIEF DESCRIPTION OF SEVERAL VIEWS OF THE DRAWINGS

Further details and advantages of the invention will become apparent from the following description of preferred embodiments of the invention and from the accompanying drawings, which show in.

DETAILED DESCRIPTION OF PREFERRED EMBODIMENTS

Embodiments of the invention are explained below with reference, by way of example, to the formation of cell aggregates from glandular stem cells on plastics nets. The implementation of the invention is, however, not restricted to the use of glandular stem cells but is also achievable with other stem cells or with other types of cells such as, for example, precursor cells or differentiated cells. The cell aggregates can include different types of cells, e.g. stem cells and first differentiated cells. Details of the culturing of stem cells or of other types of cells are not described here, since these are known per se from the standard methods of cell biology. Furthermore, other substrates can be used for forming the cell aggregates, as is described above.

Figure 1:
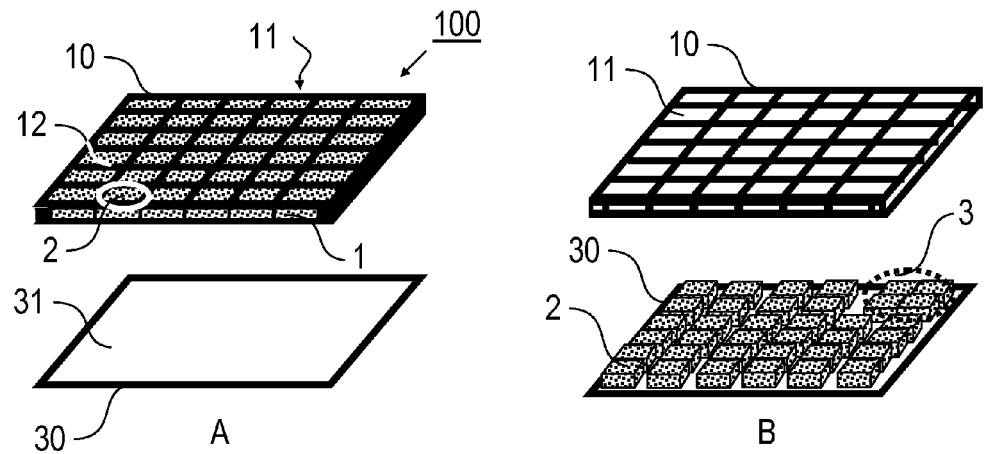
FIG. 1: a diagrammatic side view of an embodiment of the cell culturing device according to the invention and of the formation, according to the invention, of cell aggregates.

FIG. 1A shows a first embodiment of the cell culturing device 100 according to the invention, with a substrate 10 which has a plurality of substrate openings 11 and which supports a cell culture of biological cells 1 forming cell aggregates 2 in the substrate openings 11. The substrate 10 comprises e.g. a nylon net, the threads of which form the substrate elements 12 surrounding the substrate openings 11. The substrate elements 12 have a diameter of e.g. 50 µm. The side length of the substrate openings 11 (mesh width) is, for example, 0.25 mm. In FIG. 1 the cell aggregates, in particular, are shown diagrammatically. In reality the cell aggregates typically have a spherical form.

Figure 2:
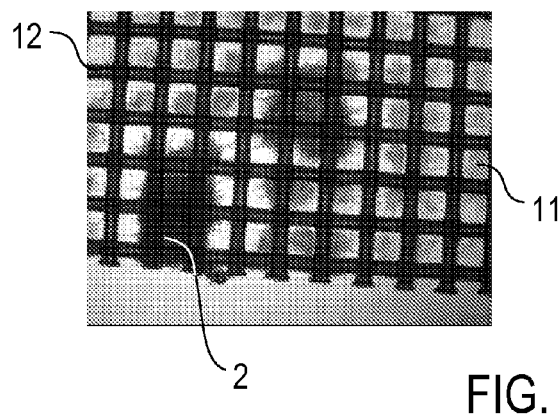
FIG. 2: a photographic representation of cell aggregates on a substrate having substrate openings.

FIG. 2 shows, by way of example, a photographic image with a plan view (partial view) of the substrate 10 used according to the invention, with the substrate openings 11 in which the cell aggregates 2 are formed. It is not mandatory for all the substrate openings 11 to contain cell aggregates 2. Some substrate openings 11 can remain free, as shown in FIG. 2.

A target substrate 30 for receiving cell aggregates 2 from the substrate 10 is illustrated in the lower portion of FIG. 1A. In this embodiment of the invention the target substrate 30 has a continuous plane substrate surface 31. The substrate 30 is made, for example, from plastic or glass.

FIG. 1B illustrates the transfer of the cell aggregates 2 from the substrate 10 onto the target substrate 30. For this the cell aggregates 2 are, individually or together, pushed out of the substrate openings 11 with a separating device (see FIGS. 3, 4) so that they fall onto the target substrate 30. Alternatively, after being pushed out of the substrate openings the cell aggregates 2 can be arranged on a surface of the substrate 10 and can be received therefrom with a slide element (not shown) and transferred to the target substrate.

Preferably only the cell aggregates are detached from the substrate openings, while cells remain on the substrate after separation. For example, individual cells, groups of cells or monolayers of the cells remain on the substrate, in particular on the substrate elements. These remaining cells (preferably stem cells) can advantageously be used for renewed overgrowth of the substrate openings.

According to the invention, the cell aggregates detached from the substrate 10 can also mutually aggregate on the target substrate 30 by means of cell contacts and can form aggregate formations 3 (illustrated diagrammatically).

Figure 3:
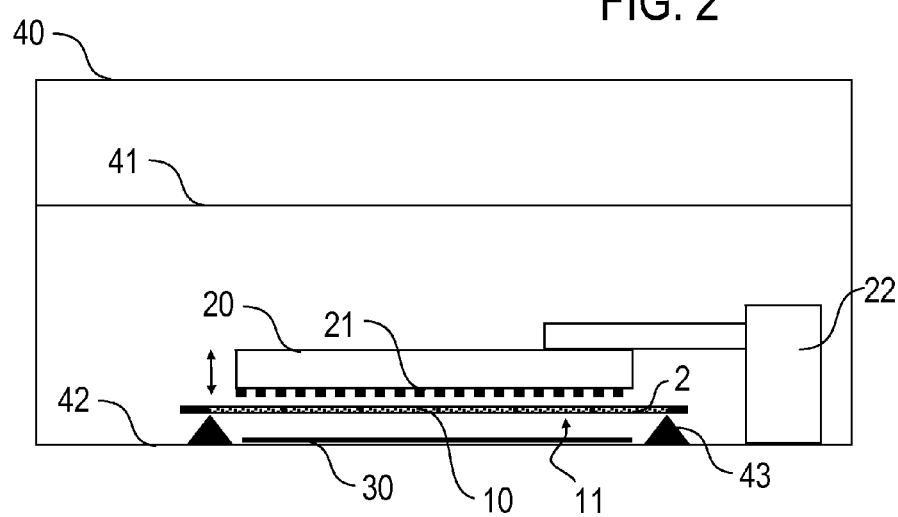
FIG. 3: a diagrammatic side view of a further embodiment of the cell culturing device according to the invention.

FIG. 3 shows a modified variant of the cell culturing device 100 according to the invention, with the substrate 10 which contains the cell aggregates 2 in the substrate openings, and with a separating device 20 having a plurality of stamping tools 21. The separating device 20 is fitted with a diagrammatically illustrated drive device 22, with which the stamping tools 21 can be inserted into the substrate openings of the substrate 10.

The cell culturing device 100 is arranged in a culturing vessel 40 containing a culturing medium 41. The substrate 10, spaced apart from the bottom 42 of the culturing vessel 40, is arranged on support elements 43. On the bottom 42 rests the target substrate 30 for receiving the cell aggregates 2.

The method, according to the invention, for culturing biological cells using the cell culturing device 100 shown in FIG. 3 comprises, for example, the following steps. First, in a growth step, growth of the cells takes place on the substrate 10. The cells overgrow the substrate openings 11. The cell aggregates 2 form in the substrate openings. In this phase the cell aggregates can include already differentiated cells. In a separation step, the cell aggregates 2 are detached from the substrate 10 using the stamping tools 21 and are transferred to the target substrate 30.

Figure 4:
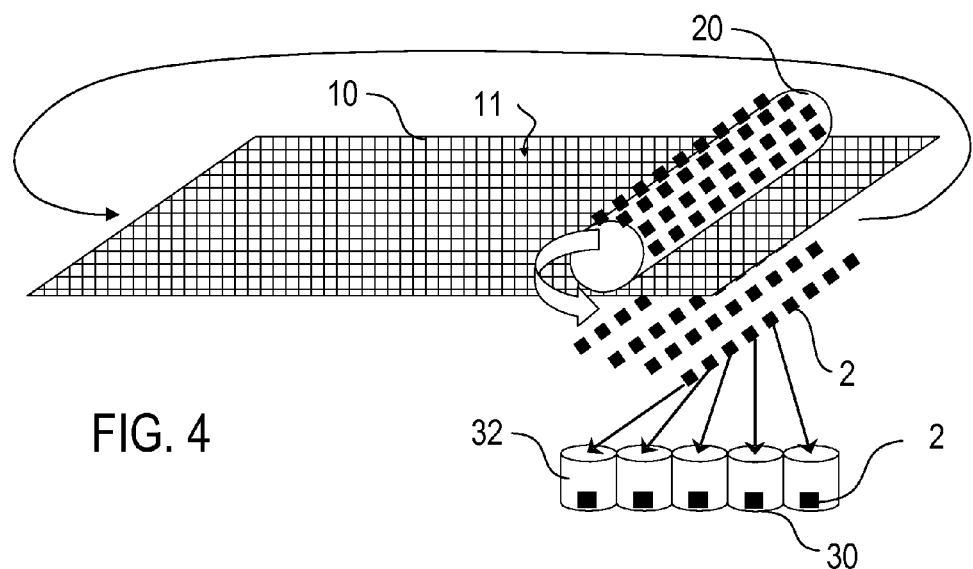
FIG. 4: a diagrammatic illustration of a further embodiment of the formation, according to the invention, of cell aggregates.

A further variant of the cell culturing according to the invention is illustrated diagrammatically in FIG. 4. On the substrate 10 the cell aggregates 2 are formed in the substrate openings 11. The separating device 20 comprises a roll, on the surface of which the stamping tools 21 are arranged. To separate the cell aggregates 2 from the substrate 10 the latter is guided past the roll, during the rotation of which the stamping tools 21 engage in the substrate openings 11 such that the cell aggregates 2 are extracted. The cell aggregates 2 are transferred to the target substrate 30 which, in this case, is shown with a plurality of individual chambers 32 or compartments.

The method illustrated in FIG. 4 can be used to achieve a cyclic process in which the substrate 10, in the form of a circulating continuous loop, is guided through a culturing medium. The substrate 10 moves through the culturing medium at such a slow speed that the required cell aggregates 2 are fully grown on reaching the separating device 20. On passing the separating device 20 the cell aggregates 2 are transferred to the target substrate 30. There follows a renewed overgrowth of the substrate openings 11 with cells which are still arranged on the substrate elements 12 following the extraction of the cell aggregates 2. The cell aggregates 2 in the chambers of the target substrate 30 shown in FIG. 4 can then be used for culturing or for testing biologically or pharmacologically active substances.

Figure 5:
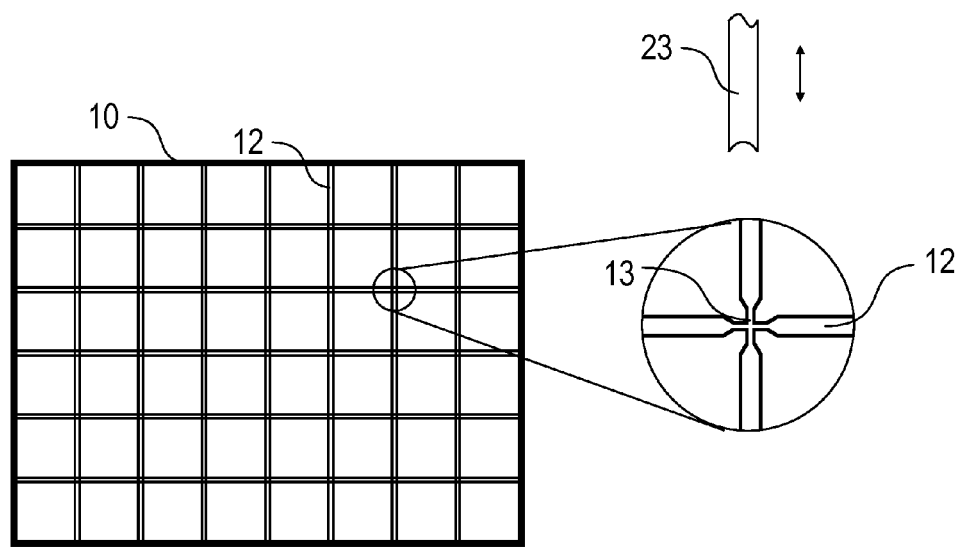
FIG. 5: a diagrammatic plan view of a further embodiment of the cell culturing device according to the invention.

FIG. 5 shows a further embodiment of the invention in which the substrate 10 comprises substrate elements 12 having predetermined breaking points 13. The breaking points 13 are formed, for example, at intersections of the substrate elements 12 in a net or lattice, as shown in the expanded cutaway portion of FIG. 5. To separate the cell aggregates (not shown in FIG. 5) from the substrate 10, the substrate elements 12 are divided at the predetermined breaking points 13 using a punching tool 23, which is shown diagrammatically.

The features of the invention disclosed in the above description, the drawings and the claims may be significant both individually and in combination for the performance of the invention in its different embodiments.

The invention claimed is:

1. A method for culturing biological cells, comprising the steps of:
   growing the cells on a substrate having a plurality of substrate openings, and
   forming cell aggregates comprising groups of cells, each of which spans one of the substrate openings, with the cell aggregates being self-supportingly arranged in the substrate openings,
   wherein the substrate comprises a net having meshes which form the substrate openings, and the substrate is spaced apart from any target substrate during the growing and forming steps.

2. The method according to claim 1, wherein a stamping tool is used for the extraction of the cell aggregates from the at least one substrate opening.

3. The method according to claim 1, wherein the substrate openings are populated with new cells after the extraction of the cell aggregates.

4. The method according to claim 3, wherein in a cyclic process the cell aggregates are repeatedly formed in the substrate openings of the substrate and extracted therefrom.

5. The method according to claim 1, wherein a separation of the cell aggregates from the substrate is provided, with the separation comprising a detachment from the substrate of substrate elements adjoining at least one substrate opening.

6. The method according to claim 1, wherein a plurality of the cell aggregates is simultaneously separated from the substrate.

7. The method according to claim 1, further comprising the steps of:
   transferring the cell aggregates onto a target substrate, and
   further culturing of the cell aggregates on the target substrate.

8. The method according to claim 7, wherein the further culturing of the cell aggregates on the target substrate comprises joining of the cell aggregates into aggregate formations.

9. The method according to claim 1, wherein the substrate has at least one of the following features:
   the substrate is made from a plastic, an inert metal or a resorbable material,
   the substrate has a thickness of less than 3 mm,
   the substrate includes substrate elements having predetermined breaking points,
   the substrate openings are formed as passing through a substrate body,
   the substrate openings are formed in a surface of a substrate body, and
   the substrate openings have a characteristic dimension smaller than 1 mm.

10. The method according to claim 1, further comprising the step of forming a predetermined aggregate shape of the cell aggregates, which shape is determined by a shape of the substrate openings.

11. The method according to claim 1, wherein the cells comprise stem cells.

12. The method according to claim 11, wherein the cells comprise adult stem cells.

13. The method according to claim 12, wherein the cells comprise glandular stem cells.

14. The method according to claim 1 wherein a separation of the cell aggregates from the substrate is provided, with the separation comprising an extraction of the cell aggregates from at least, one of the substrate openings.

* * * * *